United States Patent
Miyawaki et al.

(10) Patent No.: US 7,504,491 B2
(45) Date of Patent: Mar. 17, 2009

(54) **PIGMENT PROTEIN FROM *CNIDOPUS JAPONICUS***

(75) Inventors: Atsushi Miyawaki, Saitama (JP); Satoshi Karasawa, Tokyo (JP)

(73) Assignees: Riken, Saitama (JP); Medical and Biological Laboratories Co., Ltd., Aichi (JP)

( * ) Notice: Subject to any disclaimer, the term of this patent is extended or adjusted under 35 U.S.C. 154(b) by 79 days.

(21) Appl. No.: 10/516,317

(22) PCT Filed: Jun. 10, 2003

(86) PCT No.: PCT/JP03/07336

§ 371 (c)(1), (2), (4) Date: Sep. 26, 2005

(87) PCT Pub. No.: WO03/104460

PCT Pub. Date: Dec. 18, 2003

(65) Prior Publication Data

US 2006/0240472 A1   Oct. 26, 2006

(30) Foreign Application Priority Data

Jun. 10, 2002   (JP)   ............... 2002-168583

(51) Int. Cl.
*C07H 21/04*   (2006.01)
*C07K 1/00*   (2006.01)

(52) U.S. Cl. ..................... 536/23.1; 530/400
(58) Field of Classification Search ................ 536/23.1; 530/350, 400
See application file for complete search history.

(56) References Cited

U.S. PATENT DOCUMENTS 6,969,597 B2 * 11/2005 Lukyanov et al. .......... 435/69.1

FOREIGN PATENT DOCUMENTS

| EP | 1512744 | 3/2005 |
|---|---|---|
| EP | 1512745 | 3/2005 |
| WO | 00/34319 | 6/2000 |
| WO | 00/34526 | 6/2000 |
| WO | 01/27150 | 4/2001 |
| WO | 03/104461 | 12/2003 |
| WO | 2004/018671 | 3/2004 |

OTHER PUBLICATIONS

Ngo et al. in "The Protein Folding Problem and Tertiary Structure Prediction," 1994, Merz et al. (ed.), Birkhauser, Boston, MA, pp. 433 and 492-495.*
Lukyanov et al., US 6969597, Nov. 2005, SEQ ID No. 1 sequence alignment Result 1, database: Issued_Patents_NA.*
Lukyanov et al., US 6969597, Nov. 2005, SEQ ID No. 2 sequence alignment Result 1, database: Issued_Patents_NA.*
Chan et al., 2006, Journal of Biological Chemistry, vol. 281, No. 49, pp. 37813-37819.*
R.Y. Tsien, Ann. Rev. Biochem., vol. 67, 1998, pp. 509-544.
A. Miyawaki et al., Midoriishi, Mar. 2002, No. 13, pp. 1-4.
U.S. Appl. No. 10/516,314 to Miyawaki et al., which was filed on Dec. 10, 2004.
U.S. Appl. No. 10/525,365 to Miyawaki et al., which was filed on Feb. 23, 2005.
Hideaki Mizuno et al., "Red Fluorescent Protein from Discocoma as a Fusion Tag and a Partner for Fluorescence Resonance Energy Transfer", Biochemistry, American Chemical society, vol. 40, No. 8, pp. 2502-2510, 2001.
Y. A. Labas et al., "Diversity and evolution of the green fluorescent protein family", Proceedings of the National Academy of Science of USA, vol. 99, No. 7 pp. 4256-4261, 2002.
U.S. Appl. No. 10/516,214 to Miyawaki et al., filed Dec. 10, 2004.

* cited by examiner

*Primary Examiner*—Suzanne M. Naokes
(74) *Attorney, Agent, or Firm*—Greenblum & Bernstein, P.L.C.

(57) ABSTRACT

An object of the present invention is to provide a chromoprotein derived from *Cnidopus japonicus*. The present invention provides a chromoprotein derived from *Cnidopus japonicus* having the following properties: (1) the absorption maximum wavelength is 610 nm, and fluorescence is not emitted; (2) the molar absorption coefficient is 66,700 at 610 nm; and (3) the pH sensitivity of light-absorbing property is stable at between pH 4 and pH 10.

8 Claims, 6 Drawing Sheets

SEQUENCE LISTING

<160> NUMBER OF SEQ ID NOS: 22

<210> SEQ ID NO 1
<211> LENGTH: 232
<212> TYPE: PRT
<213> ORGANISM: cnidopus japonicus

<400> SEQUENCE: 1

```
Met Ala Ser Lys Ile Ser Asp Asn Val Arg Ile Lys Leu Tyr Met Glu
1               5                   10                  15

Gly Thr Val Asn Asn His His Phe Met Cys Glu Ala Glu Gly Glu Gly
            20                  25                  30

Lys Pro Tyr Glu Gly Thr Gln Met Glu Asn Ile Lys Val Thr Lys Gly
        35                  40                  45

Gly Pro Leu Pro Phe Ser Phe Asp Ile Leu Thr Pro Asn Cys Gln Tyr
    50                  55                  60

Gly Ser Val Ala Ile Thr Lys Tyr Thr Ser Gly Ile Pro Asp Tyr Phe
65                  70                  75                  80

Lys Gln Ser Phe Pro Glu Gly Phe Thr Trp Glu Arg Thr Thr Ile Tyr
                85                  90                  95

Glu Asp Gly Ala Tyr Leu Thr Thr Gln Gln Glu Thr Lys Leu Asp Gly
            100                 105                 110

Asn Cys Leu Val Tyr Asn Ile Lys Ile Leu Gly Cys Asn Phe Pro Pro
        115                 120                 125

Asn Gly Pro Val Met Gln Lys Lys Thr Gln Gly Trp Glu Pro Cys Cys
    130                 135                 140

Glu Met Arg Tyr Thr Arg Asp Gly Val Leu Cys Gly Gln Thr Leu Met
145                 150                 155                 160

Ala Leu Lys Cys Ala Asp Gly Asn His Leu Thr Cys His Leu Arg Thr
                165                 170                 175

Thr Tyr Arg Ser Lys Lys Ala Ala Lys Ala Leu Gln Met Pro Pro Phe
            180                 185                 190

His Phe Ser Asp His Arg Pro Glu Ile Val Lys Val Ser Glu Asn Gly
        195                 200                 205

Thr Leu Phe Glu Gln His Glu Ser Ser Val Ala Arg Tyr Cys Gln Thr
    210                 215                 220

Cys Pro Ser Lys Leu Gly His Asn
225                 230
```

<210> SEQ ID NO 2
<211> LENGTH: 699
<212> TYPE: DNA
<213> ORGANISM: cnidopus japonicus

<400> SEQUENCE: 2

```
atggcttcca aaatcagcga caatgtacgt atcaagttat atatggaggg cacagtcaac      60
aatcatcact tcatgtgcga agctgaagga gagggcaagc catacgaggg aactcaaatg     120
```

```
gagaacataa aagtcaccaa aggaggccct ctgccgttct cttttgatat cttgacgcct    180
aactgccaat atggaagcgt agccataacc aagtatacat cagggattcc agactacttt    240
aagcaatctt ttcctgaagg atttacctgg gaaagaacca caatctacga agatggggct    300
taccttacaa ctcaacaaga aaccaaactt gatggaaatt gcctcgtcta caatattaaa    360
atccttggat gtaattttcc ccccaatggt cctgtgatgc agaagaaaac ccaaggctgg    420
gaaccctgtt gcgagatgcg ctatacacgt gatggtgtgc tatgtggcca acattaatg    480 gcacttaaat gcgccgatgg gaaccacctc acttgccatc tgagaactac ttacaggtcc    540
aaaaaggcag caaaggcgtt gcagatgcca cccttccatt tttcagacca tcgtcctgaa    600
atagtgaagg tttcagagaa cggcacacta tttgaacagc acgaaagttc agtggccagg    660
tactgtcaaa catgcccatc taaacttggt cacaattaa                           699

<210> SEQ ID NO 3
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n represents inosine
<220> FEATURE:
<221> NAME/KEY: misc_feature
<222> LOCATION: (5)..(5)
<223> OTHER INFORMATION: s represents c or g
<220> FEATURE:
<221> NAME/KEY: misc_feature
<222> LOCATION: (6)..(6)
<223> OTHER INFORMATION: n represents inosine
<220> FEATURE:
<221> NAME/KEY: misc_feature
<222> LOCATION: (9)..(9)
<223> OTHER INFORMATION: n represents inosine
<220> FEATURE:
<221> NAME/KEY: misc_feature
<222> LOCATION: (10)..(10)
<223> OTHER INFORMATION: h represents a, t, or c
<220> FEATURE:
<221> NAME/KEY: misc_feature
<222> LOCATION: (12)..(12)
<223> OTHER INFORMATION: n represents inosine
<220> FEATURE:
<221> NAME/KEY: misc_feature
<222> LOCATION: (13)..(13)
<223> OTHER INFORMATION: s represents c or g
<220> FEATURE:
<221> NAME/KEY: misc_feature
<222> LOCATION: (15)..(15)
<223> OTHER INFORMATION: n represents inosine

<400> SEQUENCE: 3
ggngsnccnh tnscntt                                                    17

<210> SEQ ID NO 4
<211> LENGTH: 44
<212> TYPE: DNA
<213> ORGANISM: Artificial Sequence
<220> FEATURE:
<223> OTHER INFORMATION: primer

<400> SEQUENCE: 4
aactggaaga attcgcggcc gcagaatttt ttttttttt tttt                       44

<210> SEQ ID NO 5
<211> LENGTH: 36
```

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n represents inosine
<220> FEATURE:
<221> NAME/KEY: misc_feature
<222> LOCATION: (29)..(30)
<223> OTHER INFORMATION: n represents inosine
<220> FEATURE:
<221> NAME/KEY: misc_feature
<222> LOCATION: (34)..(35)
<223> OTHER INFORMATION: n represents inosine

<400> SEQUENCE: 5
ggccacgcgt cgactagtac gggnngggnn gggnng                                 36

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
agacgaggca atttccatca ag                                                22

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggccacgcgt cgactagtac                                                   20

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
ggctacgctt ccatattggc agtt                                              24

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
cgggatccga ccatggcttc caaaatcagc                                        30

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
ccggaattct taattgtgac caagtttaga tgggca                          36

<210> SEQ ID NO 11
<211> LENGTH: 232
<212> TYPE: PRT
<213> ORGANISM: cnidopus japonicus

<400> SEQUENCE: 11

Met Ala Ser Lys Ile Ser Asp Asn Val Arg Ile Lys Leu Tyr Met Glu
1               5                   10                  15

Gly Thr Val Asn Asn His His Phe Met Cys Glu Ala Glu Gly Glu Gly
            20                  25                  30

Lys Pro Tyr Glu Gly Thr Gln Met Glu Asn Ile Lys Val Thr Lys Gly
        35                  40                  45

Gly Pro Leu Pro Phe Ser Phe Asp Ile Leu Thr Pro Asn Cys Gln Leu
    50                  55                  60

Gly Ser Val Ala Ile Thr Lys Tyr Thr Ser Gly Ile Pro Asp Tyr Phe
65                  70                  75                  80

Lys Gln Ser Phe Pro Glu Gly Phe Thr Trp Glu Arg Thr Thr Ile Tyr
                85                  90                  95

Glu Asp Gly Ala Tyr Leu Thr Thr Gln Gln Glu Thr Lys Leu Asp Gly
            100                 105                 110

Asn Cys Leu Val Tyr Asn Ile Lys Ile Leu Gly Cys Asn Phe Pro Pro
        115                 120                 125

Asn Gly Pro Val Met Gln Lys Lys Thr Gln Gly Trp Glu Pro Cys Cys
    130                 135                 140

Glu Met Arg Tyr Thr Arg Asp Gly Val Leu Cys Gly Gln Thr Leu Met
145                 150                 155                 160

Ala Leu Lys Cys Ala Asp Gly Asn His Leu Thr Cys His Leu Arg Thr
                165                 170                 175

Thr Tyr Arg Ser Lys Lys Ala Ala Lys Ala Leu Gln Met Pro Pro Phe
            180                 185                 190

His Phe Ser Asp His Arg Pro Glu Ile Val Lys Val Ser Glu Asn Gly
        195                 200                 205

Thr Leu Phe Glu Gln His Glu Ser Ser Val Ala Arg Tyr Cys Gln Thr
    210                 215                 220

Cys Pro Ser Lys Leu Gly His Asn
225                 230

<210> SEQ ID NO 12
<211> LENGTH: 699
<212> TYPE: DNA
<213> ORGANISM: cnidopus japonicus

<400> SEQUENCE: 12
atggcttcca aaatcagcga caatgtacgt atcaagttat atatggaggg cacagtcaac      60
aatcatcact tcatgtgcga agctgaagga gagggcaagc catacgaggg aactcaaatg     120
gagaacataa agtcaccaa aggaggccct ctgccgttct cttttgatat cttgacgcct      180
aactgccaac ttggaagcgt agccataacc aagtatacat cagggattcc agactacttt    240
aagcaatctt ttcctgaagg atttacctgg gaaagaacca caatctacga agatggggct    300
taccttacaa ctcaacaaga aaccaaactt gatggaaatt gcctcgtcta caatattaaa    360
atccttggat gtaattttcc ccccaatggt cctgtgatgc agaagaaaac ccaaggctgg    420
gaaccctgtt gcgagatgcg ctatacacgt gatggtgtgc tatgtggcca aacattaatg    480

```
gcacttaaat gcgccgatgg gaaccacctc acttgccatc tgagaactac ttacaggtcc    540
aaaaaggcag caaaggcgtt gcagatgcca cccttccatt tttcagacca tcgtcctgaa    600
atagtgaagg tttcagagaa cggcacacta tttgaacagc acgaaagttc agtggccagg    660
tactgtcaaa catgcccatc taaacttggt cacaattaa                           699
```

<210> SEQ ID NO 13
<211> LENGTH: 232
<212> TYPE: PRT
<213> ORGANISM: cnidopus japonicus

<400> SEQUENCE: 13

```
Met Ala Ser Lys Ile Ser Asp Asn Val Arg Ile Lys Leu Tyr Met Glu
1               5                   10                  15

Gly Thr Val Asn Asn His His Phe Met Cys Glu Ala Glu Gly Glu Gly
                20                  25                  30

Lys Pro Tyr Glu Gly Thr Gln Met Glu Asn Ile Lys Val Thr Lys Gly
            35                  40                  45

Gly Pro Leu Pro Phe Ser Phe Asp Ile Leu Thr Pro Asn Cys Gln Met
        50                  55                  60

Gly Ser Val Ala Ile Thr Lys Tyr Thr Ser Gly Ile Pro Asp Tyr Phe
65                  70                  75                  80

Lys Gln Ser Phe Pro Glu Gly Phe Thr Trp Glu Arg Thr Thr Ile Tyr
                85                  90                  95

Glu Asp Gly Ala Tyr Leu Thr Thr Gln Gln Glu Thr Lys Leu Asp Gly
            100                 105                 110

Asn Cys Leu Val Tyr Asn Ile Lys Ile Leu Gly Cys Asn Phe Pro Pro
        115                 120                 125

Asn Gly Pro Val Met Gln Lys Lys Thr Gln Gly Trp Glu Pro Cys Cys
    130                 135                 140

Glu Met Arg Tyr Thr Arg Asp Gly Val Leu Cys Gly Gln Thr Leu Met
145                 150                 155                 160

Ala Leu Lys Cys Ala Asp Gly Asn His Leu Thr Cys His Leu Arg Thr
                165                 170                 175

Thr Tyr Arg Ser Lys Lys Ala Ala Lys Ala Leu Gln Met Pro Pro Phe
            180                 185                 190

His Phe Ser Asp His Arg Pro Glu Ile Val Lys Val Ser Glu Asn Gly
        195                 200                 205

Thr Leu Phe Glu Gln His Glu Ser Ser Val Ala Arg Tyr Cys Gln Thr
    210                 215                 220

Cys Pro Ser Lys Leu Gly His Asn
225                 230
```

<210> SEQ ID NO 14
<211> LENGTH: 699
<212> TYPE: DNA
<213> ORGANISM: cnidopus japonicus

<400> SEQUENCE: 14

```
atggcttcca aaatcagcga caatgtacgt atcaagttat atatggaggg cacagtcaac     60
aatcatcact tcatgtgcga agctgaagga gagggcaagc catacgaggg aactcaaatg    120
gagaacataa aagtcaccaa aggaggccct ctgccgttct cttttgatat cttgacgcct    180
aactgccaaa tgggaagcgt agccataacc agtatatacat cagggattcc agactacttt    240
aagcaatctt ttcctgaagg atttacctgg gaaagaacca caatctacga agatggggct    300
```

```
taccttacaa ctcaacaaga aaccaaactt gatggaaatt gcctcgtcta caatattaaa    360
atccttggat gtaattttcc ccccaatggt cctgtgatgc agaagaaaac ccaaggctgg    420
gaaccctgtt gcgagatgcg ctatacacgt gatggtgtgc tatgtggcca aacattaatg    480
gcacttaaat gcgccgatgg gaaccacctc acttgccatc tgagaactac ttacaggtcc    540
aaaaaggcag caaaggcgtt gcagatgcca cccttccatt tttcagacca tcgtcctgaa    600
atagtgaagg tttcagagaa cggcacacta tttgaacagc acgaaagttc agtggccagg    660
tactgtcaaa catgcccatc taaacttggt cacaattaa                          699
```

<210> SEQ ID NO 15
<211> LENGTH: 232
<212> TYPE: PRT
<213> ORGANISM: cnidopus japonicus

<400> SEQUENCE: 15

```
Met Ala Ser Lys Ile Ser Asp Asn Val Arg Ile Lys Leu Tyr Met Glu
1               5                   10                  15

Gly Thr Val Asn Asn His His Phe Met Cys Glu Ala Glu Gly Glu Gly
            20                  25                  30

Lys Pro Tyr Glu Gly Thr Gln Met Leu Asn Ile Lys Val Thr Lys Gly
        35                  40                  45

Gly Pro Leu Pro Phe Ser Phe Asp Ile Leu Thr Pro Asn Cys Gln Met
    50                  55                  60

Gly Ser Val Ala Ile Thr Lys Tyr Thr Ser Gly Ile Pro Asp Tyr Gly
65                  70                  75                  80

Lys Gln Ser Phe Pro Glu Gly Phe Thr Trp Glu Arg Thr Thr Ile Tyr
                85                  90                  95

Glu Asp Gly Ala Tyr Leu Thr Thr Gln Gln Glu Thr Lys Leu Asp Gly
            100                 105                 110

Asn Cys Leu Val Tyr Asn Ile Lys Ile Leu Gly Cys Asn Phe Pro Pro
        115                 120                 125

Asn Gly Pro Val Met Gln Lys Lys Thr Gln Gly Trp Glu Pro Cys Cys
    130                 135                 140

Glu Met Arg Tyr Thr Arg Asp Gly Val Leu Cys Gly Gln Thr Leu Met
145                 150                 155                 160

Ala Leu Lys Cys Ala Asp Gly Asn His Leu Thr Cys His Leu Arg Thr
                165                 170                 175

Thr Tyr Arg Ser Lys Lys Ala Ala Lys Ala Leu Gln Met Pro Pro Phe
            180                 185                 190

His Phe Ser Asp His Arg Pro Glu Ile Val Lys Val Ser Glu Asn Gly
        195                 200                 205

Thr Leu Phe Glu Gln His Glu Ser Ser Val Ala Arg Tyr Cys Gln Thr
    210                 215                 220

Cys Pro Ser Lys Leu Gly His Asn
225                 230
```

<210> SEQ ID NO 16
<211> LENGTH: 699
<212> TYPE: DNA
<213> ORGANISM: cnidopus japonicus

<400> SEQUENCE: 16

```
atggcttcca aaatcagcga caatgtacgt atcaagttat atatgctggg cacagtcaac    60
aatcatcact tcatgtgcga agctgaagga gagggcaagc catacgaggg aactcaaatg    120
```

```
cttaacataa aagtcaccaa aggaggccct ctgccgttct cttttgatat cttgacgcct   180
aactgccaat atggaagcgt agccataacc aagtatacat cagggattcc agactacggt   240
aagcaatctt ttcctgaagg atttacctgg gaaagaacca caatctacga agatggggct   300
taccttacaa ctcaacaaga aaccaaactt gatggaaatt gcctcgtcta caatattaaa   360
atccttggat gtaattttcc ccccaatggt cctgtgatgc agaagaaaac ccaaggctgg   420
gaaccctgtt gcgagatgcg ctatacacgt gatggtgtgc tatgtggcca acattaatg    480 gcacttaaat gcgccgatgg gaaccacctc acttgccatc tgagaactac ttacaggtcc   540
aaaaaggcag caaggcgtt gcagatgcca cccttccatt tttcagacca tcgtcctgaa    600
atagtgaagg tttcagagaa cggcacacta tttgaacagc acgaaagttc agtggccagg   660
tactgtcaaa catgcccatc taaacttggt cacaattaa                          699
```

<210> SEQ ID NO 17
<211> LENGTH: 232
<212> TYPE: PRT
<213> ORGANISM: cnidopus japonicus
<400> SEQUENCE: 17

```
Met Ala Ser Lys Ile Ser Asp Asn Val Arg Ile Lys Leu Tyr Met Glu
1               5                   10                  15

Gly Thr Val Asn Asn His His Phe Met Cys Glu Ala Glu Gly Glu Gly
            20                  25                  30

Lys Pro Tyr Glu Gly Thr Gln Met Glu Asn Ile Lys Val Thr Lys Gly
        35                  40                  45

Gly Pro Leu Pro Phe Ser Phe Asp Ile Leu Thr Pro Asn Cys Gln Phe
    50                  55                  60

Gly Ser Val Ala Ile Thr Lys Tyr Thr Ser Gly Ile Pro Asp Tyr Phe
65                  70                  75                  80

Lys Gln Ser Phe Pro Glu Gly Phe Thr Trp Glu Arg Thr Thr Ile Tyr
                85                  90                  95

Glu Asp Gly Ala Tyr Leu Thr Thr Gln Gln Glu Thr Lys Leu Asp Gly
            100                 105                 110

Asn Cys Leu Val Tyr Asn Ile Lys Ile Leu Gly Cys Asn Phe Pro Pro
        115                 120                 125

Asn Gly Pro Val Met Gln Lys Lys Thr Gln Gly Trp Glu Pro Cys Cys
    130                 135                 140

Glu Met Arg Tyr Thr Arg Asp Gly Val Leu Cys Gly Gln Thr Leu Met
145                 150                 155                 160

Ala Leu Lys Cys Ala Asp Gly Asn His Leu Thr Cys His Leu Arg Thr
                165                 170                 175

Thr Tyr Arg Ser Lys Lys Ala Ala Lys Ala Leu Gln Met Pro Pro Phe
            180                 185                 190

His Phe Ser Asp His Arg Pro Glu Ile Val Lys Val Ser Glu Asn Gly
        195                 200                 205

Thr Leu Phe Glu Gln His Glu Ser Ser Val Ala Arg Tyr Cys Gln Thr
    210                 215                 220

Cys Pro Ser Lys Leu Gly His Asn
225                 230
```

<210> SEQ ID NO 18
<211> LENGTH: 699
<212> TYPE: DNA
<213> ORGANISM: cnidopus japonicus

<400> SEQUENCE: 18

```
atggcttcca aaatcagcga caatgtacgt atcaagttat atatggaggg cacagtcaac    60
aatcatcact tcatgtgcga agctgaagga gagggcaagc catacgaggg aactcaaatg   120
gagaacataa aagtcaccaa aggaggccct ctgccgttct cttttgatat cttgacgcct   180
aactgccaat ttggaagcgt agccataacc aagtatacat cagggattcc agactacttt   240
aagcaatctt ttcctgaagg atttacctgg gaaagaacca caatctacga agatggggct   300
taccttacaa ctcaacaaga aaccaaactt gatggaaatt gcctcgtcta caatattaaa   360
atccttggat gtaattttcc ccccaatggt cctgtgatgc agaagaaaac ccaaggctgg   420
gaaccctgtt gcgagatgcg ctatacacgt gatggtgtgc tatgtggcca aacattaatg   480
gcacttaaat gcgccgatgg gaaccacctc acttgccatc tgagaactac ttacaggtcc   540
aaaaaggcag caaaggcgtt gcagatgcca cccttccatt tttcagacca tcgtcctgaa   600
atagtgaagg tttcagagaa cggcacacta tttgaacagc acgaaagttc agtggccagg   660
tactgtcaaa catgcccatc taaacttggt cacaattaa                          699
```

<210> SEQ ID NO 19
<211> LENGTH: 232
<212> TYPE: PRT
<213> ORGANISM: cnidopus japonicus

<400> SEQUENCE: 19

```
Met Ala Ser Lys Ile Ser Asp Asn Val Arg Ile Lys Leu Tyr Met Glu
1               5                   10                  15
Gly Thr Val Asn Asn His His Phe Met Cys Glu Ala Glu Gly Glu Gly
            20                  25                  30
Lys Pro Tyr Glu Gly Thr Gln Met Glu Asn Ile Lys Val Thr Lys Gly
        35                  40                  45
Gly Pro Leu Pro Phe Ser Phe Asp Ile Leu Thr Pro Asn Cys Gln His
    50                  55                  60
Gly Ser Val Ala Ile Thr Lys Tyr Thr Ser Gly Ile Pro Asp Tyr Phe
65                  70                  75                  80
Lys Gln Ser Phe Pro Glu Gly Phe Thr Trp Glu Arg Thr Thr Ile Tyr
                85                  90                  95
Glu Asp Gly Ala Tyr Leu Thr Thr Gln Gln Glu Thr Lys Leu Asp Gly
            100                 105                 110
Asn Cys Leu Val Tyr Asn Ile Lys Ile Leu Gly Cys Asn Phe Pro Pro
        115                 120                 125
Asn Gly Pro Val Met Gln Lys Lys Thr Gln Gly Trp Glu Pro Cys Cys
    130                 135                 140
Glu Met Arg Tyr Thr Arg Asp Gly Val Leu Cys Gly Gln Thr Leu Met
145                 150                 155                 160
Ala Leu Lys Cys Ala Asp Gly Asn His Leu Thr Cys His Leu Arg Thr
                165                 170                 175
Thr Tyr Arg Ser Lys Lys Ala Ala Lys Ala Leu Gln Met Pro Pro Phe
            180                 185                 190
His Phe Ser Asp His Arg Pro Glu Ile Val Lys Val Ser Glu Asn Gly
        195                 200                 205
Thr Leu Phe Glu Gln His Glu Ser Ser Val Ala Arg Tyr Cys Gln Thr
    210                 215                 220
Cys Pro Ser Lys Leu Gly His Asn
225                 230
```

<210> SEQ ID NO 20
<211> LENGTH: 699
<212> TYPE: DNA
<213> ORGANISM: cnidopus japonicus

<400> SEQUENCE: 20

```
atggcttcca aaatcagcga caatgtacgt atcaagttat atatggaggg cacagtcaac    60
aatcatcact tcatgtgcga agctgaagga gagggcaagc catacgaggg aactcaaatg   120
gagaacataa aagtcaccaa ggaggcccct ctgccgttct cttttgatat cttgacgcct   180
aactgccaac atggaagcgt agccataacc aagtatacat cagggattcc agactacttt   240
aagcaatctt ttcctgaagg atttacctgg gaaagaacca caatctacga agatggggct   300
taccttacaa ctcaacaaga aaccaaactt gatggaaatt gcctcgtcta caatattaaa   360
atccttggat gtaattttcc ccccaatggt cctgtgatgc agaagaaaac ccaaggctgg   420
gaaccctgtt gcgagatgcg ctatacacgt gatggtgtgc tatgtggcca acattaatg   480
gcacttaaat gcgccgatgg gaaccacctc acttgccatc tgagaactac ttacaggtcc   540
aaaaaggcag caaggcgtt gcagatgcca cccttccatt tttcagacca tcgtcctgaa   600
atagtgaagg tttcagagaa cggcacacta tttgaacagc acgaaagttc agtggccagg   660
tactgtcaaa catgcccatc taaacttggt cacaattaa                          699
```

<210> SEQ ID NO 21
<211> LENGTH: 232
<212> TYPE: PRT
<213> ORGANISM: cnidopus japonicus

<400> SEQUENCE: 21

```
Met Ala Ser Lys Ile Ser Asp Asn Val Arg Ile Lys Leu Tyr Met Glu
1               5                   10                  15

Gly Thr Val Asn Asn His His Phe Met Val Glu Ala Glu Gly Glu Gly
            20                  25                  30

Lys Pro Tyr Glu Gly Thr Gln Met Glu Asn Ile Lys Val Thr Lys Gly
        35                  40                  45

Gly Pro Leu Pro Phe Ser Phe Asp Ile Leu Thr Pro Asn Cys Gln Met
    50                  55                  60

Gly Ser Val Ala Ile Thr Lys Tyr Thr Ser Gly Ile Pro Asp Tyr Phe
65                  70                  75                  80

Lys Gln Ser Phe Pro Glu Gly Phe Thr Trp Glu Arg Thr Thr Ile Tyr
                85                  90                  95

Glu Asp Gly Ala Tyr Leu Thr Thr Gln Gln Glu Thr Lys Leu Asp Gly
            100                 105                 110

Asn Cys Leu Val Tyr Asn Ile Lys Ile Leu Gly Cys Asn Phe Pro Pro
        115                 120                 125

Asn Gly Pro Val Met Gln Lys Lys Thr Gln Gly Trp Glu Pro Ser Cys
    130                 135                 140

Glu Met Arg Tyr Thr Arg Asp Gly Val Leu Cys Gly Gln Thr Leu Met
145                 150                 155                 160

Ala Leu Lys Cys Ala Asp Gly Asn His Leu Thr Cys His Leu Arg Thr
                165                 170                 175

Thr Tyr Arg Ser Lys Lys Ala Ala Lys Ala Leu Gln Met Pro Pro Phe
            180                 185                 190

His Phe Ser Asp His Arg Leu Glu Ile Val Lys Val Ser Glu Asn Gly
        195                 200                 205
```

```
Thr Leu Phe Glu Gln His Glu Ser Ser Val Ala Arg Tyr Cys Gln Thr
    210                 215                 220

Cys Pro Ser Lys Leu Gly His Asn
225                 230

<210> SEQ ID NO 22
<211> LENGTH: 699
<212> TYPE: DNA
<213> ORGANISM: cnidopus japonicus

<400> SEQUENCE: 22
atggcttcca aaatcagcga caatgtacgt atcaagttat atatggaggg cacagtcaac        60
aatcatcact tcatggtcga agctgaagga gagggcaagc catacgaggg aactcaaatg       120
gagaacataa aagtcaccaa aggaggccct ctgccgttct cttttgatat cttgacgcct       180
aactgccaat atggaagcgt agccataacc aagtatacat cagggattcc agactacttt       240
aagcaatctt ttcctgaagg atttacctgg gaaagaacca caatctacga agatggggct       300
taccttacaa ctcaacaaga aaccaaactt gatggaaatt gcctcgtcta caatattaaa       360
atccttggat gtaattttcc ccccaatggt cctgtgatgc agaagaaaac ccaaggctgg       420
gaacccagtt gcgagatgcg ctatacacgt gatggtgtgc tatgtggcca acattaatg        480 gcacttaaat gcgccgatgg gaaccacctc acttgccatc tgagaactac ttacaggtcc       540
aaaaaggcag caaaggcgtt gcagatgcca cccttccatt tttcagacca tcgtcttgaa       600
atagtgaagg tttcagagaa cggcacacta tttgaacagc acgaaagttc agtggccagg       660
tactgtcaaa catgcccatc taaacttggt cacaattaa                              699
```

PIGMENT PROTEIN FROM *CNIDOPUS JAPONICUS*

This application is the National Stage of International Application PCT/JP03/07336, filed Jun. 10, 2003.

TECHNICAL FIELD

The present invention relates to a novel chromoprotein. More specifically, the present invention relates to a novel chromoprotein derived from *Cnidopus japonicus*, and the use thereof.

BACKGROUND ART

Green fluorescent protein (GFP) derived from *Aequorea Victoria*, a jellyfish, has many purposes in biological systems. Recently, various GFP mutants have been produced based on the random mutagenesis and semi-rational mutagenesis, wherein a color is changed, a folding property is improved, luminance is enhanced, or pH sensitivity is modified. Fluorescent proteins such as GFP are fused with other proteins by gene recombinant technique, and monitoring of the expression and transportation of the fusion proteins is carried out.

One of the most commonly used types of GFP mutant is Yellow fluorescent protein (YFP). Among Aequorea-derived GFP mutants, YFP exhibits the fluorescence with the longest wavelength. The values $\epsilon$ and $\Phi$ of the majority of YEPs are 60,000 to 100,000 $M^{-1}cm^{-1}$ and 0.6 to 0.8, respectively (Tsien, R. Y. (1998). Ann. Rev. Biochem. 67, 509-544). These values are comparable to those of the general fluorescent group (fluorescein, rhodamine, etc.). Accordingly, improvement of the absolute luminance of YFP is nearly approaching its limit.

In addition, cyan fluorescent protein (CFP) is another example of the GFP mutant. Of this type of protein, ECFP (enhanced cyan fluorescent protein) has been known. Moreover, red fluorescent protein (RFP) has been isolated from sea anemone (*Discoma* sp.). Of this type of protein, DasRed has been known. Thus, 4 types of fluorescent proteins, that are, green fluorescent protein, yellow fluorescent protein, cyan fluorescent protein, and red fluorescent protein, have successively been developed. The range of the spectrum has significantly been expanded.

DISCLOSURE OF THE INVENTION

An object of the present invention is to provide a novel chromoprotein derived from *Cnidopus japonicus*.

The present inventors have conducted intensive studies directed towards achieving the aforementioned object. They have designed suitable primers based on information regarding the amino acid sequences of known fluorescent proteins. Using these primers, they have succeeded in the amplification and cloning of a gene encoding a novel chromoprotein from the cDNA library of *Cnidopus japonicus* exhibiting a green color. The present inventors have further analyzed the light-absorbing properties and pH sensitivity of the obtained chromoprotein derived from *Cnidopus japonicus*. The present invention has been completed based on these findings.

That is to say, the present invention provides a chromoprotein derived from *Cnidopus japonicus* having the following properties:

(1) the absorption maximum wavelength is 610 nm, and fluorescence is not emitted;

(2) the molar absorption coefficient is 66,700 at 610 nm; and (3) the pH sensitivity of light-absorbing property is stable at between pH 4 and pH 10.

In another aspect, the present invention provides a chromoprotein having either one of the following amino acid sequences:

(a) the amino acid sequence shown in SEQ ID NO: 1; and (b) an amino acid sequence comprising a deletion, substitution and/or addition of one or several amino acids with respect to the amino acid sequence shown in SEQ ID NO: 1, and having light-absorbing properties.

In another aspect, the present invention provides a chromoprotein capable of emitting fluorescence, which has an amino acid sequence, wherein, with respect to the amino acid sequence shown in SEQ ID NO: 1, alanine as an amino acid residue at position 28 is substituted by glycine, glutamic acid as an amino acid residue at position 41 is substituted by methionine, cysteine as an amino acid residue at position 145 is substituted by serine, and threonine as an amino acid residue at position 158 is substituted by isoleucine.

In another aspect, the present invention provides:

a chromoprotein having an amino acid sequence wherein tyrosine as an amino acid residue at position 64 is substituted by leucine with respect to the amino acid sequence shown in SEQ ID NO: 1;

a chromoprotein having an amino acid sequence wherein tyrosine as an amino acid residue at position 64 is substituted by methionine with respect to the amino acid sequence shown in SEQ ID NO: 1;

a chromoprotein having an amino acid sequence, wherein glutamic acid as an amino acid residue at position 41 is substituted by leucine, and phenylalanine as an amino acid residue at position 80 is substituted by glycine, with respect to the amino acid sequence shown in SEQ ID NO: 1;

a chromoprotein capable of emitting fluorescence, which has an amino acid sequence wherein tyrosine as an amino acid residue at position 64 is substituted by phenylalanine with respect to the amino acid sequence shown in SEQ ID NO: 1;

a chromoprotein capable of emitting fluorescence, which has an amino acid sequence wherein tyrosine as an amino acid residue at position 64 is substituted by histidine with respect to the amino acid sequence shown in SEQ ID NO: 1; and a chromoprotein capable of emitting fluorescence, which has an amino acid sequence, wherein cysteine as an amino acid residue at position 26 is substituted by valine, cysteine as an amino acid residue at position 143 is substituted by serine, and proline as an amino acid residue at position 199 is substituted by leucine, with respect to the amino acid sequence shown in SEQ ID NO: 1.

In another aspect, the present invention provides DNA encoding the protein of the present invention.

In another aspect, the present invention provides either one of the following DNAs:

(a) DNA encoding the amino acid sequence shown in SEQ ID NO: 1; and (b) DNA encoding an amino acid sequence, which comprises a deletion, substitution and/or addition of one or several amino acids with respect to the amino acid sequence shown in SEQ ID NO: 1, and has light-absorbing properties.

In another aspect, the present invention provides DNA having either one of the following nucleotide sequences:

(a) the nucleotide sequence shown in SEQ ID NO: 2; and (b) a nucleotide sequence comprising a deletion, substitution and/or addition of one or several nucleotides with respect to the nucleotide sequence shown in SEQ ID NO: 2, and encoding a protein having light-absorbing properties.

In another aspect, the present invention provides DNA having the nucleotide sequence shown in any one of SEQ ID NOS: 12, 14, 16, 18, 20, or 22.

In another aspect, the present invention provides a recombinant vector having the DNA of the present invention.

In another aspect, the present invention provides a transformant having the DNA or recombinant vector of the present invention.

In another aspect, the present invention provides a fusion protein composed of the chromoprotein of the present invention and another protein.

In another aspect, the present invention provides a method for analyzing a physiologically active substance, which is characterized in that the FRET (fluorescence resonance energy transfer) method is applied using the chromoprotein of the present invention as an acceptor protein.

In another aspect, the present invention provides a light-absorbing reagent kit comprising the chromoprotein, DNA, recombinant vector, transformant, or fusion protein of the present invention.

BEST MODE FOR CARRYING OUT THE INVENTION

Figure 1:
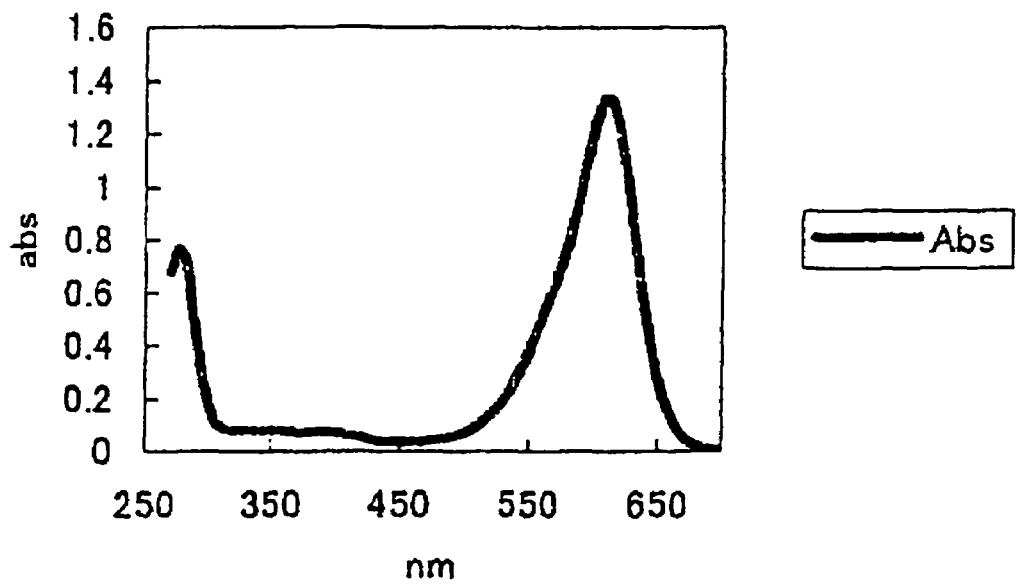
FIG. 1 shows the results obtained by measuring the absorption spectrum of the chromoprotein (KGr) derived from *Cnidopus japonicus* of the present invention. The transverse axis indicates the wavelength of absorbed light, and the vertical axis indicates absorbance.

The embodiments of the present invention will be described in detail below.

(1) Chromoprotein of the Present Invention

The chromoprotein of the present invention is characterized in that it is derived from *Cnidopus japonicus*, and has the following properties:

(1) the absorption maximum wavelength is 610 nm, and fluorescence is not emitted;
(2) the molar absorption coefficient is 66,700 at 610 nm; and
(3) the pH sensitivity of light-absorbing property is stable at between pH 4 and pH 10.

*Cnidopus japonicus* is one type of sea anemone belonging to Anthozoa of Cnidaria. Among the types of sea anemone that can be seen in Japan, *Cnidopus japonicus* has the highest degree of color mutation. Its withers height is always low, and it has a large number of warts on the body wall thereof. It has approximately 200 short tentacles. A parent sea anemone discharges developed embryos from its oral part. The discharged embryos become attached to the body wall of the parent sea anemone. Thereafter, the embryos are further developed, and as a result, they become baby sea anemone. Thus, this sea anemone was named Komochi Isoginchaku (a Japanese name meaning "seed sea anemone"). This type of sea anemone is distributed in the intertidal zones on the rock coasts between Hokkaido and Boso Peninsula and also in the zones immediately below the intertidal zones.

It is to be noted that a chromoprotein having the aforementioned properties was isolated using *Cnidopus japonicus* as a starting material in the examples described later, but that the chromoprotein of the present invention may also be obtained from forms of sea anemone other than *Cnidopus japonicus* in some cases. Such a chromoprotein is also included in the scope of the present invention.

As described in the examples below, the chromoprotein of the present invention has an absorption maximum wavelength of 610 nm and does not emit fluorescence. In addition, the present chromoprotein has a molar absorption coefficient of 66,700 at 610 nm. The molar absorption coefficient represents the amount of absorbed photons per mole of molecule. Since the chromoprotein of the present invention does not emit fluorescence, the chromoprotein of the present invention can be used: (1) as an acceptor molecule (energy receptor) in FRET; (2) in development of a system for converting the energy of applied light into energy other than the light; and (3) in introduction of a mutation into the amino acid sequence of the protein to modify it so that it emits fluorescence.

In addition, the chromoprotein of the present invention is characterized in that the pH sensitivity of light-absorbing properties is stable at between pH 4 and pH 10. That is to say, in the case of the chromoprotein of the present invention, the peak value of the absorption spectrum does not significantly fluctuate in the range between pH 4 and pH 10. Accordingly, even under the same conditions, the chromoprotein of the present invention can be used in a broad range of pH environments, and thus, the use of the chromoprotein in vivo has few restrictions.

The examples of the chromoprotein of the present invention include a chromoprotein having either one of the following amino acid sequences:

(a) the amino acid sequence shown in SEQ ID NO: 1; and
(b) an amino acid sequence comprising a deletion, substitution and/or addition of one or several amino acids with respect to the amino acid sequence shown in SEQ ID NO: 1, and having light-absorbing properties.

The scope of "one or several" in the phrase "an amino acid sequence comprising a deletion, substitution and/or addition of one or several amino acids" is not particularly limited in the present specification. For example, it means 1 to 20, preferably 1 to 10, more preferably 1 to 7, further preferably 1 to 5, and particularly preferably 1 to 3.

The term "light-absorbing properties" is used in the present specification to mean properties capable of absorbing light having a certain wavelength. For example, an absorption maximum wavelength may be 610 nm as in the case of the chromoprotein described in the present specification, or the value of the absorption maximum wavelength may also be shifted. It is preferable that the pH sensitivity of light-absorbing properties is stable at between pH 4 and pH 10.

The chromoprotein of the present invention having the amino acid sequence shown in SEQ ID NO: 1 in the sequence listing does not emit fluorescence. In the present invention, one or several amino acids are deleted, substituted, and/or added with respect to the amino acid sequence shown in SEQ ID NO: 1, so as to produce a protein having modified light-absorbing properties, or so as to produce a protein emitting fluorescence in some cases. The thus produced proteins are also included in the scope of the present invention.

A specific example of a fluorescent protein produced by such mutation of amino acids may be a fluorescent protein having an amino acid sequence, wherein, with respect to the amino acid sequence shown in SEQ ID NO: 1, alanine as an amino acid residue at position 28 is substituted by glycine, glutamic acid as an amino acid residue at position 41 is substituted by methionine, cysteine as an amino acid residue at position 145 is substituted by serine, and threonine as an amino acid residue at position 158 is substituted by isoleucine.

Other specific examples of a fluorescent protein produced by such mutation of amino acids may include: a chromoprotein having an amino acid sequence wherein tyrosine as an amino acid residue at position 64 is substituted by leucine with respect to the amino acid sequence shown in SEQ ID NO: 1; a chromoprotein having an amino acid sequence wherein tyrosine as an amino acid residue at position 64 is substituted by methionine with respect to the amino acid sequence shown in SEQ ID NO: 1; a chromoprotein having an amino acid sequence, wherein glutamic acid as an amino acid residue at position 41 is substituted by leucine, and phenylalanine as an amino acid residue at position 80 is substituted by glycine, with respect to the amino acid sequence shown in SEQ ID NO: 1; a chromoprotein capable of emitting fluorescence, which has an amino acid sequence wherein tyrosine as an amino acid residue at position 64 is substituted by phenylalanine with respect to the amino acid sequence shown in SEQ ID NO: 1; a chromoprotein capable of emitting fluorescence, which has an amino acid sequence wherein tyrosine as an amino acid residue at position 64 is substituted by histidine with respect to the amino acid sequence shown in SEQ ID NO: 1; and a chromoprotein capable of emitting fluorescence, which has an amino acid sequence, wherein cysteine as an amino acid residue at position 26 is substituted by valine, cysteine as an amino acid residue at position 143 is substituted by serine, and proline as an amino acid residue at position 199 is substituted by leucine, with respect to the amino acid sequence shown in SEQ ID NO: 1.

The method of obtaining the chromoprotein of the present invention is not particularly limited. The protein may be either a protein synthesized by chemosynthesis, or recombinant protein produced by a gene recombination technique.

Where a recombinant protein is produced, it is necessary to obtain DNA encoding the protein. Appropriate primers are designed by using information regarding the amino acid sequence shown in SEQ ID NO: 1 of the sequence listing of the present specification and the nucleotide sequence shown in SEQ ID NO: 2 thereof. Using these primers, PCR is carried out by using cDNA library derived from *Cnidopus japonicus* as a template, so that DNA encoding the chromoprotein of the present invention can be obtained. The chromoprotein of the present invention can be produced by introducing this DNA into an appropriate expression system. Expression in an expression system will be described later in the present specification.

(2) DNA of the Present Invention

According to the present invention, a gene encoding the chromoprotein of the present invention is provided.

Specific examples of DNA encoding the chromoprotein of the present invention may include either one of the following DNAs:

(a) DNA encoding the amino acid sequence shown in SEQ ID NO: 1; and
(b) DNA encoding an amino acid sequence, which comprises a deletion, substitution and/or addition of one or several amino acids with respect to the amino acid sequence shown in SEQ ID NO: 1, and has light-absorbing properties.

Other examples of DNA encoding the chromoprotein of the present invention may include either one of the following DNAs:

(a) the nucleotide sequence shown in SEQ ID NO: 2; and
(b) a nucleotide sequence comprising a deletion, substitution and/or addition of one or several nucleotides with respect to the nucleotide sequence shown in SEQ ID NO: 2, and encoding a protein having light-absorbing properties.

Further, examples of the DNA having the nucleotide sequence comprising a deletion, substitution and/or addition of one or several nucleotides with respect to the nucleotide sequence shown in SEQ ID NO: 2, and encoding a protein having light-absorbing properties, may include DNA having the nucleotide sequence shown in any one of SEQ ID NOS: 12, 14, 16, 18, 20, or 22.

The DNA of the present invention can be synthesized by, for example, the phosphoamidite method, or it can also be produced by polymerase chain reaction (PCR) using specific primers. The DNA of the present invention is produced by the method described above in the specification.

A method of introducing a desired mutation into a certain nucleic acid sequence is known to a person skilled in the art. For example, known techniques such as a site-directed mutagenesis, PCR using degenerated oligonucleotides, or the exposure of cells containing nucleic acid to mutagens or radioactive rays, are appropriately used, so as to construct DNA having a mutation. Such known techniques are described in, for example, Molecular Cloning: A Laboratory Manual, $2^{nd}$ Ed., Cold Spring Harbor Laboratory, Cold Spring Harbor, N.Y., 1989; and Current Protocols in Molecular Biology, Supplements 1 to 38, John Wiley & Sons (1987-1997).

(3) Recombinant Vector of the Present Invention

The DNA of the present invention can be inserted into a suitable vector and used. The type of a vector used in the present invention is not particularly limited. For example, it may be either a vector that can autonomously replicate (e.g., a plasmid, etc.), or vector that is incorporated into the genomes of host cells when it is introduced into the host cells and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows a transcriptional activity in host cells, and it is appropriately selected depending on the type of host cells.

Examples of a promoter which can operate in bacterial cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage rhamda, and lac, trp and tac promoters of *Escherichia coli*.

Examples of a promoter which can operate in mammalian cells may include an SV40 promoter, an MT-1 (metallothionein gene) promoter, and an adenovirus-2 major late promoter. Examples of a promoter which can operate in insect cells may include a polyhedrin promoter, a P10 promoter, an *Autographa californica* polyhedrosis basic protein promoter, a baculovirus immediate-early gene 1 promoter, and a baculovirus 39K delayed-early gene promoter. Examples of a promoter which can be operate in yeast host cells may include promoters derived from yeast glycolytic genes, an alcohol dehydrogenase gene promoter, a TPI1 promoter, and an ADH2-4c promoter.

Examples of a promoter which can operate in filamentous cells may include an ADH3 promoter and a tpiA promoter.

In addition, an appropriate terminator such as a human growth hormone terminator, or a TPI1 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent from host cells, such as a dihydrofolate reductase (DHFR) gene or a *Shizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(4) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria, yeasts, fungal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells. A method of transforming mammalian cells and expressing the introduced DNA sequence in the cells is also known. Examples of such a method may include the electroporation, the calcium phosphate method, and the lipofection method.

Examples of yeast cells may include those belonging to *Saccharomyces* or *Shizosaccharomyces*. Examples of such cells may include *Saccharomyces cerevisiae* and *Saccharomyces kluyveri*. Examples of a method of introducing a recombinant vector into yeast host cells may include the electroporation, the spheroplast method, and the lithium acetate method.

Examples of other fungal cells may include those belonging to Filamentous fungi such as *Aspergillus, Neurospora, Fusarium* or *Trichoderma*. Where Filamentous fungi are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus infecting to insects belonging to *Barathra brassicae*, can be used as baculovirus.

Examples of insect cells used herein may include Sf9 and Sf21, which are *Spodoptera frugiperda* ovarian cells [Baculovirus Expression Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus may include the calcium phosphate method and the lipofection method.

The above transformant is cultured in an appropriate nutritive medium under conditions enabling the introduced DNA construct to be expressed. In order to isolate and purify the protein of the present invention from the culture product of the transformant, common methods of isolating and purifying proteins may be used.

For example, where the protein of the present invention is expressed in a state dissolved in cells, after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

(5) Use of the Chromoprotein of the Present Invention and a Fusion Protein Comprising the Same The chromoprotein of the present invention can be fused with another protein, so as to construct a fusion protein. The type of said another protein to be fused to the chromoprotein of the present invention is not particularly limited, and preferred examples may include a protein which interacts with another molecule. The examples may include a receptor protein or ligand thereof, antigen, antibody and the like.

A method of obtaining the fusion protein of the present invention is not particularly limited. It may be either a protein synthesized by chemosynthesis, or recombinant protein produced by a gene recombination technique.

Where a recombinant fusion protein is produced, it is necessary to obtain DNA encoding the protein. The DNA encoding the chromoprotein of the present invention and the DNA encoding the another protein to be fused to the chromoprotein, can be obtained by the method as mentioned above in this specification or by the method similar to it. Then, these DNA fragments are ligated to one another by a gene recombination technique, so that DNA encoding the desired fusion protein can be obtained. This DNA is then introduced into an appropriate expression system, so that the fusion protein of the present invention can be produced.

FRET (fluorescence resonance energy transfer) has been known as a means for analyzing the interaction between molecules. In FRET, for example, a first molecule labeled with a cyan fluorescent protein (CFP) acting as a first fluorescent protein is allowed to coexist with a second molecule labeled with a yellow fluorescent protein (YFP) acting as a second fluorescent protein, so as to allow the yellow fluorescent protein (YFP) to act as an acceptor molecule and to allow the cyan fluorescent protein (CFP) to act as a donor molecule. Thus, FRET (fluorescence resonance energy transfer) is allowed to take place between both molecules, so as to visualize the interaction between the first and second molecules. Namely, in FRET, different dyes are introduced into two types of molecules. One dyes with a higher energy level (a donor molecule) is selectively excited, and the fluorescence of the dye is measured. Long-wavelength fluorescence from the other dye (an acceptor molecule) is also measured. The interaction between the molecules is visualized by using the difference between the amounts of both fluorescences. Only when both dyes are adjacent to each other due to the interaction of the two types of molecules, a decrease in the fluorescence of the donor molecule and an increase in the fluorescence of the acceptor molecule are observed by single wavelength excitation dual wavelength photometry. However, in a case where a chromoprotein is used as an acceptor molecule, a decrease in the fluorescence of the donor molecule occurs only when both dyes are adjacent to each other by the interaction of the two types of molecules. Such a decrease can be observed by single wavelength excitation single wavelength photometry. Thus, the use of the chromoprotein of the present invention enables facilitation of measurement apparatuses.

The chromoprotein of the present invention is particularly advantageous when it is used as an acceptor molecule in FRET (fluorescence resonance energy transfer). That is to say, a fused form (a first fused form) of the chromoprotein of the present invention and a test substance is first produced. Then, a fused form (a second fused form) of another test substance interacting with the above test substance and another fluorescent protein is produced. Thereafter, the first fused form is allowed to interact with the second fused form, and the generated fluorescence is analyzed, so that the interaction between the aforementioned two types of test substances can be analyzed. FRET (fluorescence resonance energy transfer) using the chromoprotein of the present invention may be carried out either in a test tube or in a cell.

(6) Kit of the Present Invention

The present invention provides a light-absorbing reagent kit comprising at least one which is selected from the chromoprotein, fusion protein, DNA, recombinant vector or transformant, which are described in the present specification. The kit of the present invention can be produced from commonly used materials that are known per se, by using common methods.

Reagents such as the chromoprotein or the DNA are dissolved in an appropriate solvent, so that the reagents can be prepared in a form suitable for conservation. Water, ethanol, various types of buffer solution, etc. can be used as such a solvent.

The present invention will be further described in the following examples. However, the present invention is not limited by these examples.

EXAMPLES

Example 1

Isolation of Gene Encoding Novel Chromoprotein from Sea Anemone (1) Extraction of Total RNA A chromoprotein gene was isolated from sea anemone emitting a green color. *Cnidopus japonicus* emitting a green color was used as a material. Frozen *Cnidopus japonicus* was crushed in a mortar. 7.5 ml of "TRIzol" (GIBCO BRL) was added to 1 g (wet weight) of *Cnidopus japonicus*, and the mixture was homogenized, followed by centrifugation at 1,500×g for 10 minutes. 1.5 ml of chloroform was added to the supernatant. The mixture was stirred for 15 seconds and then left at rest for 3 minutes. The resultant product was centrifuged at 7,500×g for 15 minutes. 3.75 ml of isopropanol was added to the supernatant. The mixture was stirred for 15 seconds and then left at rest for 10 minutes. The resultant product was centrifuged at 17,000×g for 10 minutes. The supernatant was discarded, and 6 ml of 70% ethanol was added thereto. The obtained mixture was centrifuged at 17,000×g for 10 minutes. The supernatant was discarded, and the precipitate was dissolved in 200 μl of DEPC water. Total RNA dissolved in the DEPC water was 100 times diluted, and the values of O.D.260 and O.D.280 were measured, so as to determine the concentration of RNA. 1.2 mg of the total RNA was obtained from a green individual.

(2) Synthesis of First Stand cDNA cDNA (33 µl) was synthesized from 4 µg of the total RNA using a kit for synthesizing first strand cDNA, "Ready To Go" (Amersham Pharmacia).

(3) Degenerated PCR

Using 3 µl out of the synthesized first strand cDNA (33 µl) as a template, PCR was carried out. Primers were designed and produced by comparing the amino acid sequences of known fluorescent proteins, extracting similar portions, and converting them into nucleotide sequences. The sequences of the used primers are shown below:

```
5'-GGNGSNCCNHTNSCNTT-3';          (primer 1)  (SEQ ID NO: 3)

and

5'-AACTGGAAGAATTCGCGGCCGCAGAATTTTTTTTTTTTTTTT-3',  (primer 2)  (SEQ ID NO: 4)
``` wherein N represents inosine, S represents C or G, and H represents A, T, or C.

| Composition of PCR reaction solution | |
|---|---|
| Template (first strand cDNA) | 3 µl |
| X 10 taq buffer | 5 µl |
| 2.5 mM dNTPs | 4 µl |
| 100 uM primer 3 | 1 µl |
| 100 uM primer 4 | 1 µl |
| Milli Q | 35 µl |
| Taq polymerase (5 U/µl) | 1 µl |

RCR Reaction Conditions
94° C., 1 minute (PAD)
94° C., 30 seconds (denaturation)
52° C., 30 seconds (annealing of the primers to the template)
72° C., 1 minute (elongation of the primers)

30 cycles consisting of the above 3 steps were carried out. The annealing temperature was decreased 0.3° C. per cycle. That is to say, the annealing temperature in the 30$^{th}$ cycle was 43° C.

72° C., 7 minutes (final elongation)
Retention at 4° C.

Using 1 µl of an amplified product obtained as a result of the first PCR reaction as a template, PCR was carried out once again under the same conditions. A 800-bp fragment (derived from the green individual) was cut out by agarose gel electrophoresis and then purified. This 800-bp fragment contained a 3'-UTR portion as a whole.

(4) Subcloning and Sequencing

The purified DNA fragment was ligated to a pT7-blue vector (Novagen). Escherichia coli (TG1) was transformed with the vector, and the obtained transformants were subjected to blue white selection. Thereafter, plasmid DNA was purified from white colonies of Escherichia coli. The nucleotide sequence of the inserted DNA fragment was determined by a DNA sequencer. The obtained nucleotide sequence was compared with the nucleotide sequences of other fluorescent protein genes to confirm that the nucleotide sequence of the DNA was derived from a fluorescent protein. 5'-RACE and 3'-RACE methods were applied to a gene that had been confirmed to be a part of a fluorescent protein gene, so as to carry out the cloning of a full-length gene.

(5) 5'-RACE Method

In order to determine the nucleotide sequence of the 5'-terminal side of the DNA fragment obtained by degenerated PCR, the 5'-RACE method was applied using 5'-RACE System for Rapid Amplification of cDNA Ends, Version 2.0 (GIBCO BRL). 3 µg of the total RNA prepared in (1) above was used as a template.

For the first amplification of DC-tailed cDNA of the green individual, the following primers were used:

```
                                                    (SEQ ID NO: 5)
5'-GGCCACGCGTCGACTAGTACGGGNNGGGNNGGGNNG-3';
(primer 3)

and (SEQ ID NO: 6)
5'-AGACGAGGCAATTTCCATCAAG-3',
(primer 4)
``` wherein N represents inosine.

For the second amplification, the following primers were used:

```
                                   (SEQ ID NO: 7)
5'-GGCCACGCGTCGACTAGTAC-3';        (primer 5)

and (SEQ ID NO: 8)
5'-GGCTACGCTTCCATATTGGCAGTT-3'.    (primer 6)
```

PCR reaction conditions and the like were determined in accordance with the protocols attached with the kit.

The 350-bp amplified band was cut out by agarose gel electrophoresis and then purified. The purified DNA fragment was ligated to a pT7-blue vector (Novagen). Escherichia coli (TG1) was transformed with the vector, and the obtained transformants were subjected to blue white selection. Thereafter, plasmid DNA was purified from white colonies of Escherichia coli. The nucleotide sequence of the inserted DNA fragment was determined by a DNA sequencer. The entire nucleotide sequence is shown in SEQ ID NO: 2, and the entire amino acid sequence is shown in SEQ ID NO: 1.

Example 2

Expression of Protein in Escherichia coli

Primers corresponding to the N- and C-termini of the protein were produced from the obtained full-length nucleotide sequence. PCR was carried out using the primers and the first strand cDNA prepared in (2) above as a template. The used primers are as follows:

```
                                                            (SEQ ID NO: 9)
5'-CGGGATCCGACCATGGCTTCCAAAATCAGC-3';
(primer 7)

and (SEQ ID NO: 10)
5'-CCGGAATTCTTAATTGTGACCAAGTTTAGATGGGCA-3'.
(primer 8)
```

| Composition of PCR reaction solution | |
|---|---|
| Template (first strand cDNA) | 3 μl |
| X 10 pyrobest buffer | 5 μl |
| 2.5 mM dNTPs | 4 μl |
| 100 μM primer 7 | 1 μl |
| 100 μM primer 8 | 1 μl |
| Milli Q | 35 μl |
| Pyrobest polymerase (5 U/μl) | 1 μl |

RCR Reaction Conditions
94° C., 1 minute (PAD)
94° C., 30 seconds (denaturation)
55° C., 30 seconds (annealing of the primers to the template)
72° C., 1 minute (elongation of the primers)
 30 cycles consisting of the above 3 steps were carried out.
72° C., 7 minutes (final elongation)
Retention at 4° C.

An amplified band of approximately 700 bp was cut out by agarose gel electrophoresis and then purified. The purified DNA fragment was subcloned into the BamHI-EcoRI site of a pRSET vector (Invitrogen), and it was then allowed to express in *Escherichia coli* (JM109-DE3). Since the expressed protein was constructed such that His-tag was attached to the N-terminus thereof, it was purified with Ni-Agarose gel (QIAGEN). Purification was carried out in accordance with the attached protocols.

Example 3

Analysis of Protein (1) Analysis of Light-absorbing Properties

The light-absorbing properties of the protein expressed in Example 2 were analyzed.

An absorption spectrum was measured using a 50 mM HEPES solution (pH 7.5) containing a 20 μM chromoprotein. A molar absorption coefficient was calculated from the peak value of this spectrum. In the case of the chromoprotein derived from the green individual (referred to as KGr), the absorption peak was observed at 610 nm, and no fluorescence was detected (Table 1, FIG. 1).

TABLE 1

| Properties of chromoprotein (KGr) | | | | | |
|---|---|---|---|---|---|
| Absorption maximum | Fluorescence maximum | Molar absorption coefficient | quantum yield | pH sensitivity | Number of amino acids |
| 610 nm | — | 66,700 (610 nm) | — | Non | 232 |

(1) Measurement of pH Sensitivity

The pH sensitivity of the protein expressed in Example 2 was analyzed.

Figure 2:
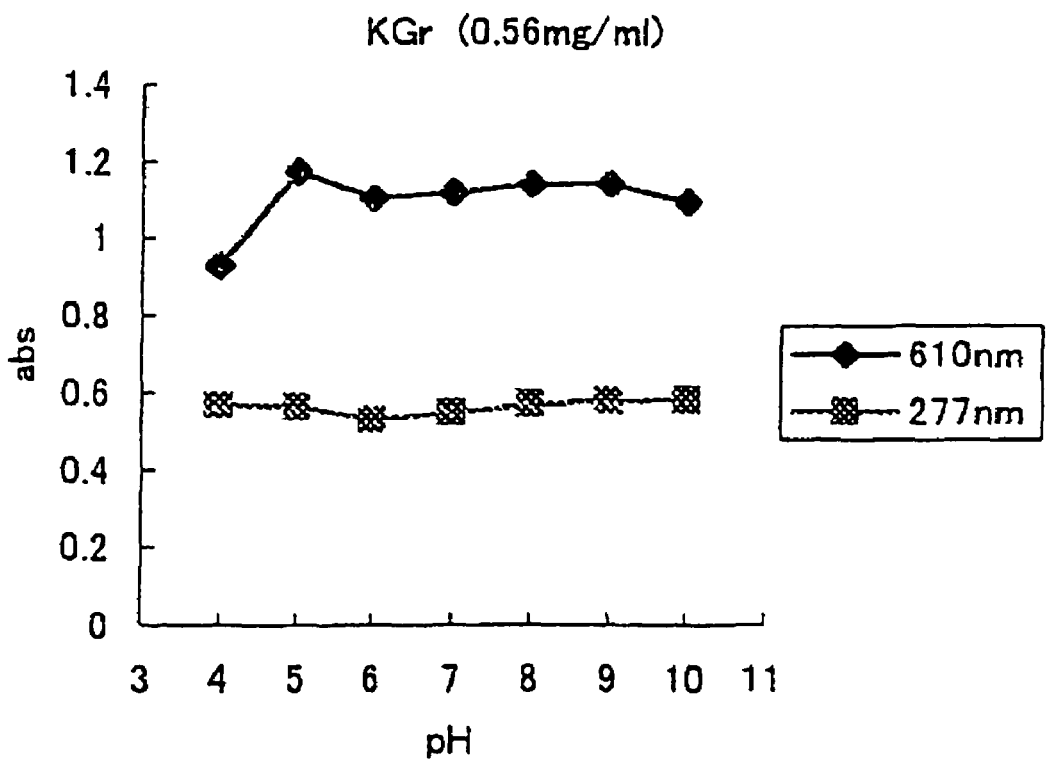
FIG. 2 shows the pH sensitivity of the absorption spectrum of the chromoprotein (KGr) derived from *Cnidopus japonicus* of the present invention. The transverse axis indicates pH value, and the vertical axis indicates absorbance. 610 nm indicates the absorbance that is specific to the chromoprotein (KGr) derived from *Cnidopus japonicus* of the present invention, and 277 nm indicates the absorbance (light absorption by aromatic amino acids) that is generally used as a quantitative amount of protein. In other words, it is shown that the amount of protein is constant at 277 nm, and the absorbance at 610 nm that is specific to the chromoprotein (KGr) derived from *Cnidopus japonicus* of the present invention hardly changes in the range between pH 4 and pH 10.

The absorption spectrum of the protein was measured in the following 100 mM buffer solution (FIG. 2).

The following buffer solutions were used for each pH:
pH 4 and 5: Acetate buffer
pH 6: MES buffer
pH 7 and 8: HEPES buffer
pH 9 and 10: Glycine buffer The peak value did not significantly change at any pH.

Example 4

Modification of KGr

Figure 3:
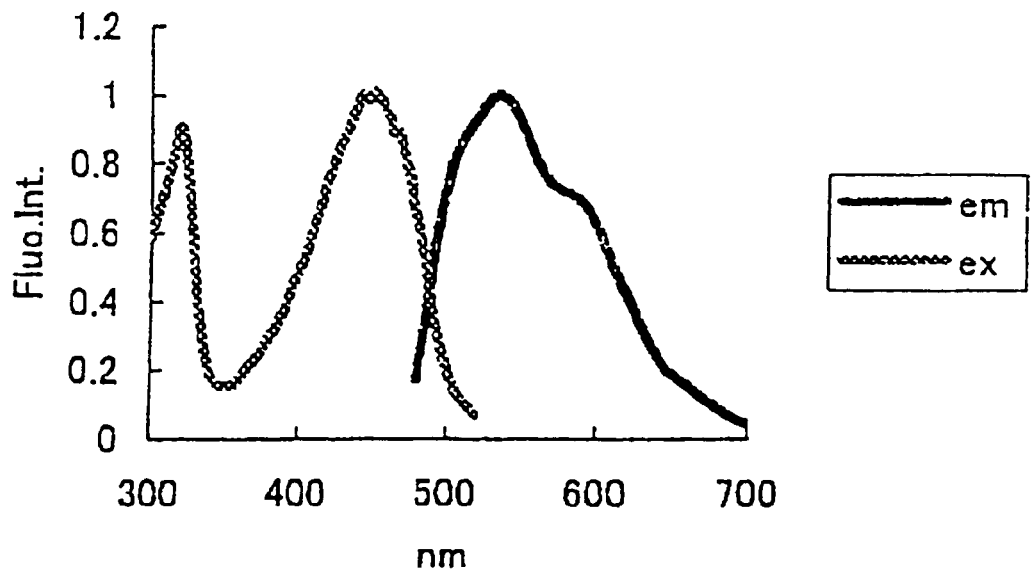
FIG. 3 shows the fluorescence spectrum of a mutant of the chromoprotein (KGr) derived from *Cnidopus japonicus* of the present invention (a mutant obtained by substituting A at position 28 by G, substituting E at position 41 by M, substituting C at position 145 by S, and substituting T at position 158 by I in the amino acid sequence of KGr). The transverse axis indicates wavelength, and the vertical axis indicates fluorescence intensity. The term "em" indicates a fluorescence spectrum, and the term "ex" indicates an excitation spectrum.

In KGr, A at position 28 was substituted by G, E at position 41 was substituted by M, C at position 145 was substituted by S, and T at position 158 was substituted by I, so that the KGr was modified to have an absorption peak at 444 nm and to emit yellow fluorescence with a peak at 534 nm (FIG. 3).

Example 5

Modification of Properties of KGr by Amino Acid Substitution

Y at position 64 that is a chromophore-forming amino acid (QYG) of KGr was substituted by L or M, so that the absorption peak became 418 nm and so that the absorption peak was shifted from the original absorption peak at 610 nm to the shorter wavelength side (FIGS. 1 and 2). The amino acid sequence of the protein wherein Y at position 64 was substituted by L is shown in SEQ ID NO: 11, and the nucleotide sequence thereof is shown in SEQ ID NO: 12. The amino acid sequence of the protein wherein Y at position 64 was substituted by M is shown in SEQ ID NO: 13, and the nucleotide sequence thereof is shown in SEQ ID NO: 14.

E at position 41 was substituted by L, and F at position 80 was substituted by G, so that the absorption peak become 528 nm and so that the absorption peak was shifted from the original absorption peak at 610 nm to the shorter wavelength side (FIG. 3). The amino acid sequence of this protein is shown in SEQ ID NO: 15, and the nucleotide sequence thereof is shown in SEQ ID NO: 16.

Figure 4:
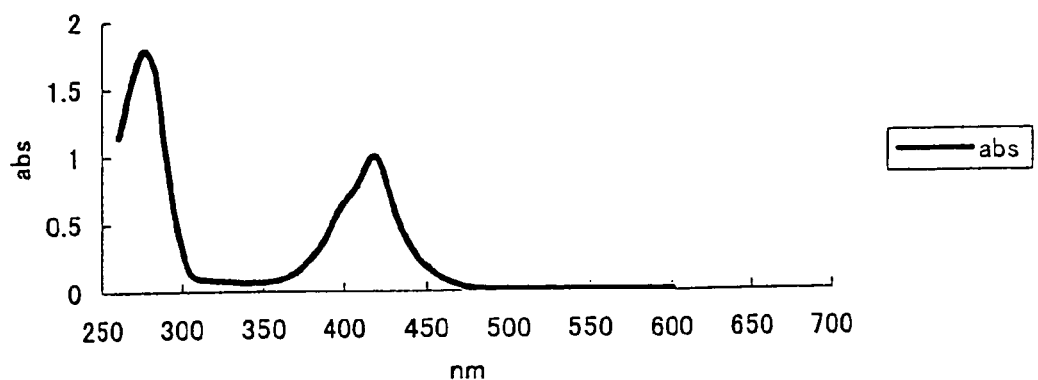
FIG. 4 shows the absorption spectrum of a mutant of the chromoprotein (KGr) derived from *Cnidopus japonicus* of the present invention (a mutant obtained by substituting Y at position 64 by L in the amino acid sequence of KGr).
Figure 5:
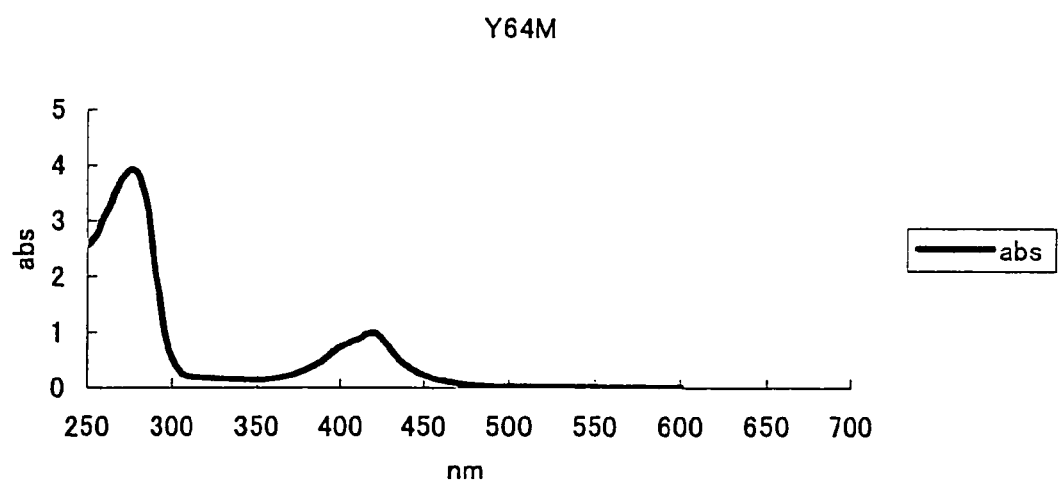
FIG. 5 shows the absorption spectrum of a mutant of the chromoprotein (KGr) derived from *Cnidopus japonicus* of the present invention (a mutant obtained by substituting Y at position 64 by M in the amino acid sequence of KGr).

Y at position 64 that is a chromophore-forming amino acid (QYG) was substituted by F, so that the absorption peak became 412 nm, and so that the absorption peak was shifted from the original absorption peak at 610 nm to the shorter wavelength side and the protein was further modified to emit fluorescence with a peak at 504 nm (FIGS. 4 and 5). The amino acid sequence of this protein is shown in SEQ ID NO: 17, and the nucleotide sequence thereof is shown in SEQ ID NO: 18.

Figure 6:
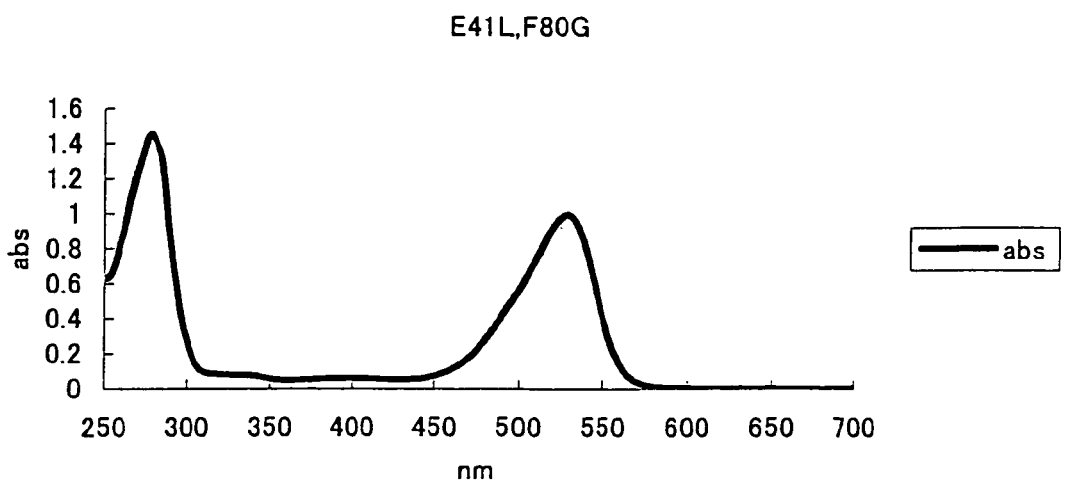
FIG. 6 shows the absorption spectrum of a mutant of the chromoprotein (KGr) derived from *Cnidopus japonicus* of the present invention (a mutant obtained by substituting E at position 41 by L and substituting F at position 80 by G in the amino acid sequence of KGr).
Figure 7:
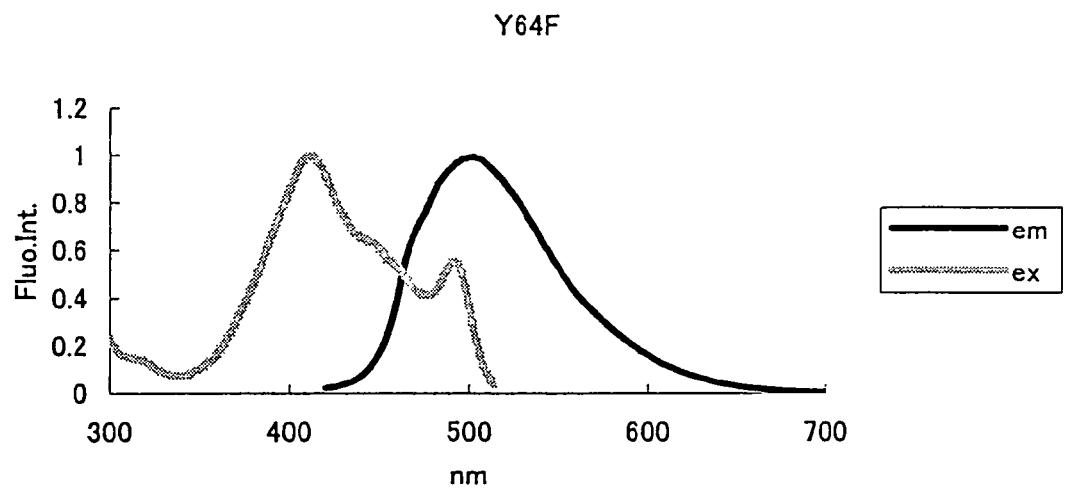
FIG. 7 shows the fluorescence and excitation spectrums of a mutant of the chromoprotein (KGr) derived from *Cnidopus japonicus* of the present invention (a mutant obtained by substituting Y at position 64 by F in the amino acid sequence of KGr).

Y at position 64 that is a chromophore-forming amino acid (QYG) was substituted by H, so that the absorption peak became 418 nm, and so that the absorption peak was shifted from the original absorption peak at 610 nm to the shorter wavelength side and the protein was further modified to emit fluorescence with a peak at 520 nm (FIGS. 6 and 7). The amino acid sequence of this protein is shown in SEQ ID NO: 19, and the nucleotide sequence thereof is shown in SEQ ID NO: 20.

Figure 8:
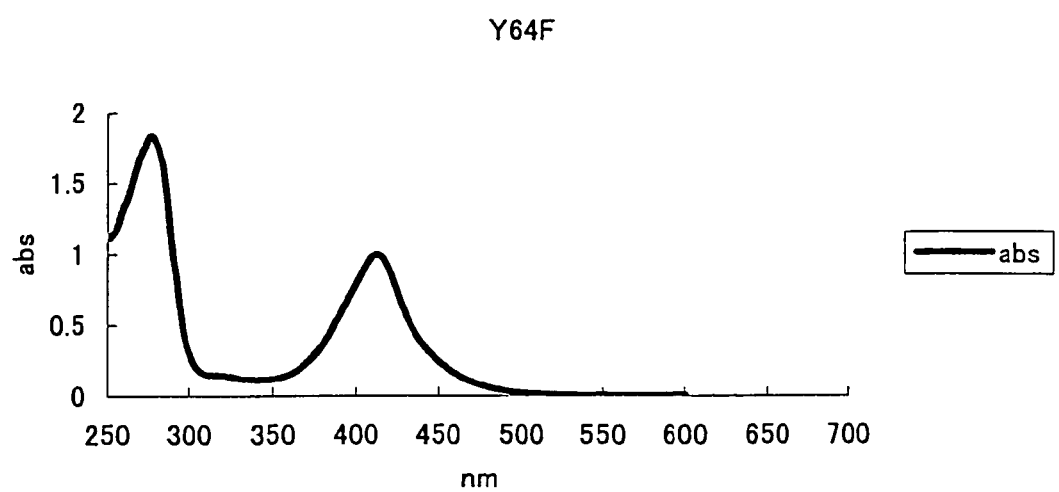
FIG. 8 shows the absorption spectrum of a mutant of the chromoprotein (KGr) derived from *Cnidopus japonicus* of the present invention (a mutant obtained by substituting Y at position 64 by F in the amino acid sequence of KGr).
Figure 9:
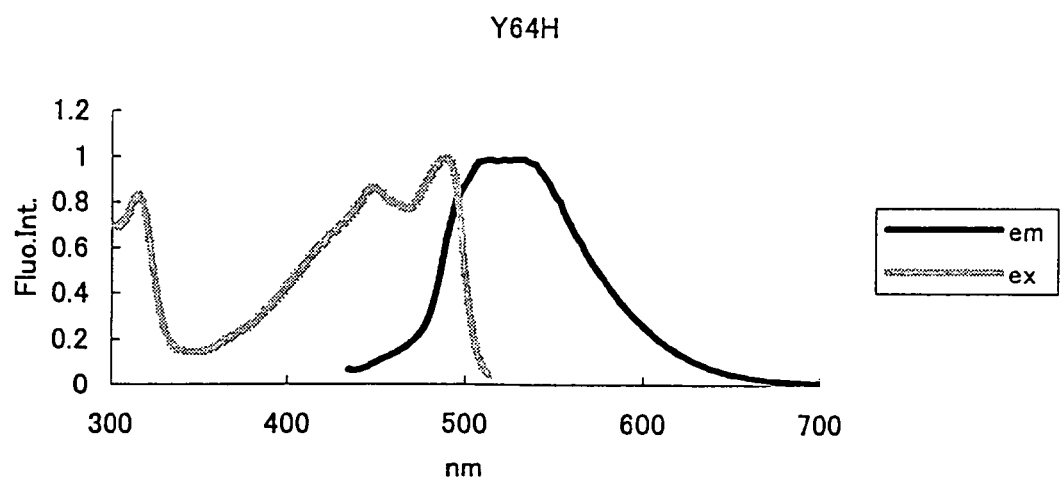
FIG. 9 shows the fluorescence and excitation spectrums of a mutant of the chromoprotein (KGr) derived from *Cnidopus japonicus* of the present invention (a mutant obtained by substituting Y at position 64 by H in the amino acid sequence of KGr).
Figure 10:
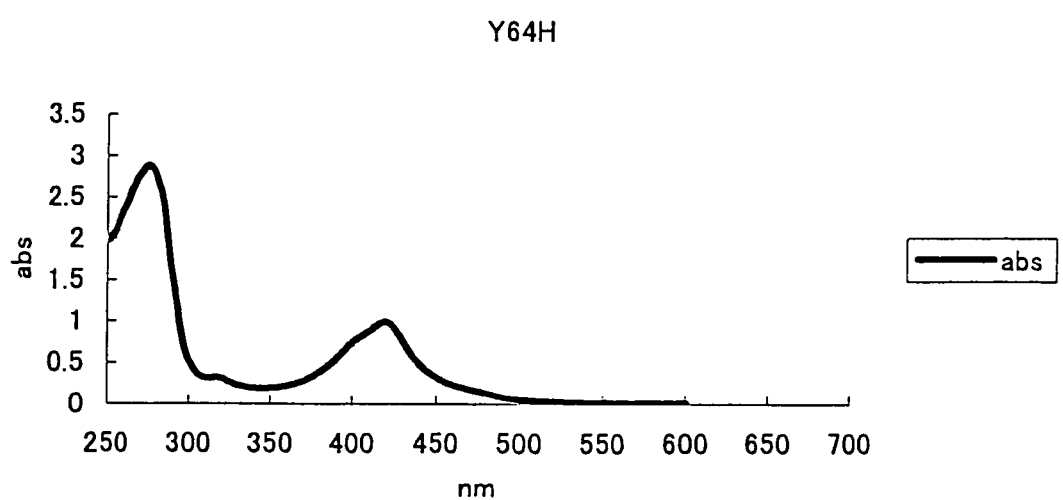
FIG. 10 shows the absorption spectrum of a mutant of the chromoprotein (KGr) derived from *Cnidopus japonicus* of the present invention (a mutant obtained by substituting Y at position 64 by H in the amino acid sequence of KGr).
Figure 11:
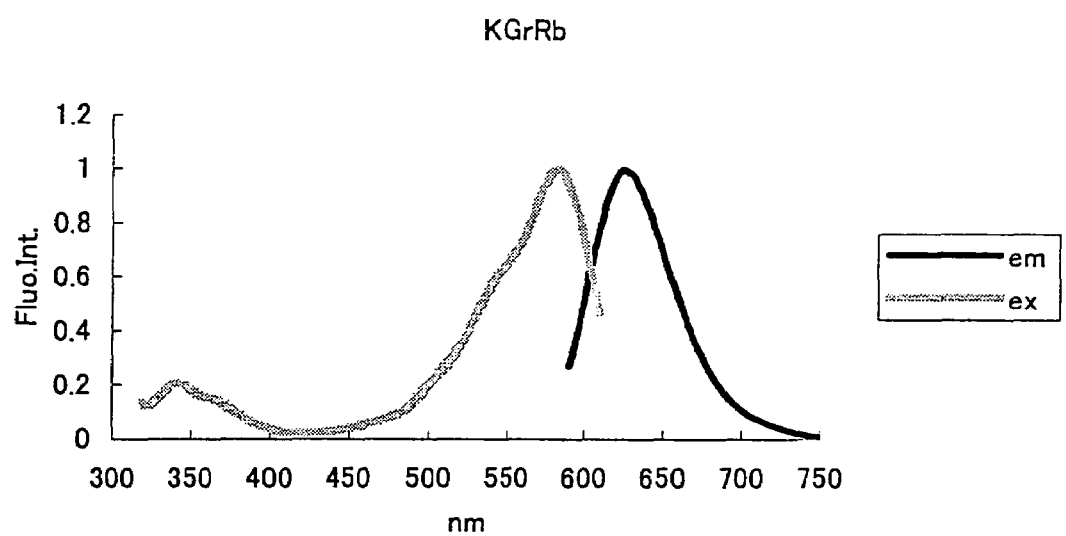
FIG. 11 shows the fluorescence and excitation spectrums of a mutant of the chromoprotein (KGr) derived from *Cnidopus japonicus* of the present invention (a mutant obtained by substituting C at position 26 by V, substituting C at position 143 by S, and substituting P at position 199 by L in the amino acid sequence of KGr).
Figure 12:
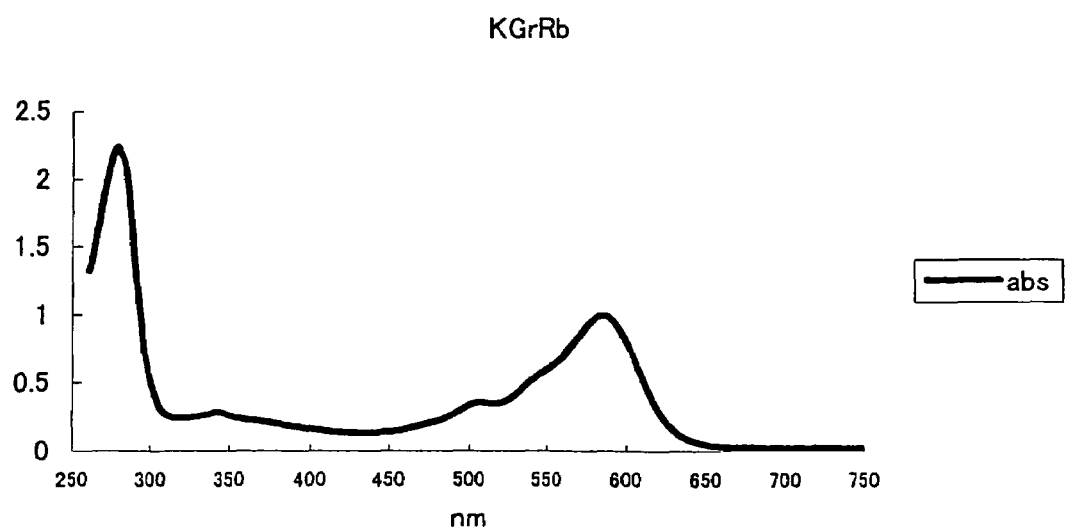
FIG. 12 shows the absorption spectrum of a mutant of the chromoprotein (KGr) derived from *Cnidopus japonicus* of the present invention (a mutant obtained by substituting C at position 26 by V, substituting C at position 143 by S, and substituting P at position 199 by L in the amino acid sequence of KGr).

C at position 26 was substituted by V, C at position 143 was substituted by S, and P at position 199 was substituted by L, so that the absorption peak became 585 nm, and so that the absorption peak was shifted from the original absorption peak at 610 nm to the shorter wavelength side and the protein was further modified to emit fluorescence with a peak at 625 nm. This fluorescent protein was defined as KGr Rb (FIGS. 8 and 9). The amino acid sequence of this protein is shown in SEQ ID NO: 21, and the nucleotide sequence thereof is shown in SEQ ID NO: 22.

INDUSTRIAL APPLICABILITY

The present invention provides a novel chromoprotein derived from *Cnidopus japonicus*. The chromoprotein of the present invention has desired fluorescence properties and low pH sensitivity. Thus, it is useful for molecular biology analysis.

---

The invention claimed is:

1. An isolated DNA of either one of the following:
   (a) DNA encoding the amino acid sequence shown in SEQ ID NO: 1, wherein said SEQ ID NO: 1 has light absorbing properties but does not emit fluorescence, or
   (b) DNA encoding the amino acid sequence shown in SEQ ID NO: 1, which further comprises a deletion, substitution and/or addition of one to ten amino acids and has modified light-absorbing properties and/or emits fluorescence.

2. An isolated DNA having the nucleotide sequence shown in SEQ ID NO: 2.

3. An isolated DNA having the nucleotide sequence shown in any one of SEQ ID NOS: 12, 14, 16, 18, 20, or 22.

4. A recombinant vector having the DNA of claim 1.

5. An isolated transformant comprising the DNA of claim 1 or a recombinant vector having the DNA of claim 1.

6. A light-absorbing reagent kit comprising the isolated DNA of claim 1.

7. A light-absorbing reagent kit comprising the recombinant vector of claim 4.

8. A light-absorbing reagent kit comprising the isolated transformant of claim 5.

* * * * *